United States Patent [19]
Dennision

[11] Patent Number: 5,412,560
[45] Date of Patent: May 2, 1995

[54] METHOD FOR EVALUATING AND ANALYZING FOOD CHOICES

[75] Inventor: Darwin Dennison, Amherst, N.Y.

[73] Assignee: Dine Systems, Inc., Amherst, N.Y.

[21] Appl. No.: 964,531

[22] Filed: Oct. 20, 1992

Related U.S. Application Data

[63] Continuation-in-part of Ser. No. 671,146, Aug. 27, 1991, abandoned.

[51] Int. Cl.$^6$ .............................................. G06F 15/00
[52] U.S. Cl. ............................ 364/413.01; 364/413.29
[58] Field of Search ...................... 364/413.01, 413.29, 364/709.03; 434/262

[56] References Cited

U.S. PATENT DOCUMENTS

| | | | |
|---|---|---|---|
| 4,095,274 | 6/1978 | Gordon | 364/709.03 |
| 4,212,079 | 7/1980 | Segar et al. | 364/413.29 |
| 4,321,674 | 3/1982 | Krames et al. | 364/413.29 |
| 4,464,122 | 8/1984 | Fuller et al. | 434/262 |
| 4,855,945 | 8/1989 | Sakai | 364/413.29 |
| 4,891,756 | 1/1990 | Williams, III | 364/413.29 |
| 4,911,256 | 3/1990 | Attikiouzel | 364/709.03 |
| 4,951,197 | 8/1990 | Mellinger | 364/413.01 |

OTHER PUBLICATIONS

"Deal-A-Meal" Advertisement, *Parade* newspaper supplement, Oct. 31, 1993, p. 7.
N-Squared Computing, "Nutritionist III", 3040 Commerical St. SE, Suit 240; Salem, Oregon 97302.
N-Squared Computing, "The Right Byte", 3040 Commercial St. SE, Suit 240; Salem, Oregon 97302.
"Trim Tech", Jul. 1, 1989; 330 E. New York St. Aurora, Ill. 60505 USA.
U.S. Dept. of Agriculture, U.S. Dept. of Health and Human Services, *Dietary Guidelines for Americans*, Oct., 1990.
Dennison, Dennison, and Frank, *The DINE System: Improving Food Choices of the Public*, Jan., 1993.
Select Committee on Nutrition and Human Needs, *Dietary Goals for the United States*, Second Edition, Dec., 1977.
Subcommittee on the Tenth Edition of the RDA's, *Recommended Dietary Allowances*, 10th Edition, 1989.
Welch, Davis, and Shaw, *A Brief History of Food Guides in the United States*, Nov./Dec., 1992.
Welch, Davis, and Shaw, *Development of the Food Guide Pyramid*, Nov./Dec., 1992.
Hudnall and Wellman, *Missing the Nutrition Message of Balance, Variety and Moderation*, Nov./Dec., 1992.

*Primary Examiner*—Gail O. Hayes
*Assistant Examiner*—X. Chunk-Trans
*Attorney, Agent, or Firm*—Jon L. Roberts; Thomas M. Champagne; Roberts & Associates

[57] ABSTRACT

A process for evaluation of an individual's food choices based upon selected factors and dietary guidelines is disclosed. The DINE System provides a method and apparatus which allows an individual to determine how well or poorly the person is eating. The invention analyzes the food an individual eats and determines certain predictor and follower nutrients that will give rise to an assessment of how a person's diet matches with various dietary guidelines established by governmental and/or other entities. The invention provides the results of the analysis to the individual complete with messages regarding over or under consumption of key nutrients so that the individual can correct the diet thereby resulting in better eating habits. The invention also gives the individual a "score" by which the person can immediately assess how well he or she is doing with respect to the various guidelines. The higher the number the better the diet.

10 Claims, 17 Drawing Sheets

MACRONUTRIENTS/COMPONENTS

| PREDICTOR | FOLLOWER |
|---|---|
| PROTEIN | VITAMINS B1, B2, B6, B12, D, AND K, BIOTIN, COPPER, CHROMIUM, COBALT, ESSENTIAL AND NON-ESSENTIAL AMINO ACIDS, FOLACIN, MANGANESE, MAGNESIUM, NIACIN, PANTOTHENIC ACID, PHOSPHORUS, SELENIUM, SULFUR, AND ZINC |
| SATURATED FAT | NONE |
| MONOUNSATURATED FAT | BIOTIN |
| POLYUNSATURATED FAT | BIOTIN, VITAMIN E, LINOLEIC ACID, OLEIC ACID |
| COMPLEX CARBOHYDRATES | VITAMINS B1, B6 AND K, CHROMIUM, COPPER, FOLACIN, MAGNESIUM, MANGANESE, MOLYBDENUM, NIACIN, PANTOTHENIC ACID, PHOSPHORUS |
| DIETARY FIBER | B-VITAMINS, COMPLEX CARBOHYDRATES |
| SUGAR | NONE |

MICRONUTRIENTS/COMPONENTS

| PREDICTOR | FOLLOWER |
|---|---|
| CHOLESTEROL | BIOTIN |
| SODIUM | CHLORIDE, IODINE |
| POTASSIUM | FIBER, VITAMIN C |
| VITAMIN A | FIBER, VITAMIN C, POTASSIUM |
| VITAMIN C | FIBER, VITAMIN A, POTASSIUM |
| IRON | PROTEIN, PHOSPHORUS, B-VITAMINS, CHROMIUM, COPPER, SELENIUM, ZINC |
| CALCIUM | VITAMIN D, PROTEIN, RIBOFLAVIN, PHOSPHORUS, POTASSIUM, MAGNESIUM |
| PHOSPHORUS | CALCIUM, PROTEIN, VITAMIN D, RIBOFLAVIN, NIACIN, B12, POTASSIUM, MAGNESIUM, CHROMIUM, COPPER, SELENIUM, ZINC |

MACRONUTRIENTS/COMPONENTS

| PREDICTOR | FOLLOWER |
|---|---|
| PROTEIN | VITAMINS B1, B2, B6, B12, D, AND K, BIOTIN, COPPER, CHROMIUM, COBALT, ESSENTIAL AND NON-ESSENTIAL AMINO ACIDS, FOLACIN, MANGANESE, MAGNESIUM, NIACIN, PANTOTHENIC ACID, PHOSPHORUS, SELENIUM, SULFUR, AND ZINC |
| SATURATED FAT | NONE |
| MONOUNSATURATED FAT | BIOTIN |
| POLYUNSATURATED FAT | BIOTIN, VITAMIN E, LINOLEIC ACID, OLEIC ACID |
| COMPLEX CARBOHYDRATES | VITAMINS B1, B6 AND K, CHROMIUM, COPPER, FOLACIN, MAGNESIUM, MANGANESE, MOLYBDENUM, NIACIN, PANTOTHENIC ACID, PHOSPHORUS |
| DIETARY FIBER | B-VITAMINS, COMPLEX CARBOHYDRATES |
| SUGAR | NONE |

MICRONUTRIENTS/COMPONENTS

| PREDICTOR | FOLLOWER |
|---|---|
| CHOLESTEROL | BIOTIN |
| SODIUM | CHLORIDE, IODINE |
| POTASSIUM | FIBER, VITAMIN C |
| VITAMIN A | FIBER, VITAMIN C, POTASSIUM |
| VITAMIN C | FIBER, VITAMIN A, POTASSIUM |
| IRON | PROTEIN, PHOSPHORUS, B-VITAMINS, CHROMIUM, COPPER, SELENIUM, ZINC |
| CALCIUM | VITAMIN D, PROTEIN, RIBOFLAVIN, PHOSPHORUS, POTASSIUM, MAGNESIUM |
| PHOSPHORUS | CALCIUM, PROTEIN, VITAMIN D, RIBOFLAVIN, NIACIN, B12, POTASSIUM, MAGNESIUM, CHROMIUM, COPPER, SELENIUM, ZINC |

*FIG. 1*

FOOD CHOICE ENVIROMENT
FOOD RECORD (FOR EXAMPLE)

| | | | | |
|---|---|---|---|---|
| BRK | 2086 | 1.00 | ROL | DANISH PASTRY, CINNAMON RAISIN, INDIVIDUAL, SARA LEE |
| BRK | 1723 | 1.00 | CUP | COFFEE, BREWED |
| BRK | 1753 | 1.00 | TBS | COFFEE WHITENER, NON-DAIRY, LIQUID, FARM RICH |
| BRK | 5255 | 1.00 | CBE | SUGAR, WHITE, GRANULATED (1/2 IN CUBES) |
| LUN | 945 | 2.00 | SLC | BREAD, WHEAT, BRICK OVEN, ARNOLD |
| LUN | 2757 | 0.50 | CUP | FISH/SEAFOOD, TUNA SALAD, PREP W/SALAD DRESSING |
| LUN | 3451 | 1.00 | LF | LETTUCE, LOOSELEAF, RAW |
| LUN | 5403 | 2.00 | SLC | TOMATOES, RAW (2-3/5 IN DIA) |
| LUN | 4027 | 1.00 | FRT | PEARS, RAW (2-1/2 IN DIA x 3-1/2 IN LONG) |
| LUN | 732 | 12.00 | OZF | BEVERAGES, CARBONATED, COCA-COLA |
| DRN | 3914 | 1.50 | CUP | PASTA, SPAGHETTI, COOKED W/O SALT, FIRM STAGE |
| DRN | 4878 | 0.50 | CUP | SAUCE, SPAGHETTI, PLAIN & W/MUSH, HOMESTYLE, RAGU |
| DRN | 3755 | 5.00 | VEG | MUSHROOMS, RAW, WHOLE, COOKED, BOILED, DRAINED |
| DRN | 3861 | 0.25 | CUP | ONIONS, RAW, WHOLE, COOKED, BOILED, DRAINED |
| DRN | 5217 | 0.50 | CUP | SQUASH, SUMMER, ZUCCHINI, RAW, SLICED, BOILED |
| DRN | 907 | 1.00 | SLC | BREAD, ITALIAN (4-1/2 x 3-1/4 x 3/4) |
| DRN | 3603 | 2.00 | TSP | MARGARINE, TUB, CORN OIL, FLEISCHMANN'S |

*FIG. 3*

INDIVIDUAL ENVIROMENT

SAMPLE PERSON

PERSONAL INFORMATION (FOR EXAMPLE)

| | |
|---|---|
| SEX: | FEMALE |
| AGE: | 36 YEARS |
| HEIGHT: | 5'5" |
| WEIGHT: | 130 LBS |
| DESIRED WEIGHT: | 120 LBS |
| FRAME SIZE: | MEDIUM |
| ACTIVITY LEVEL: | BELOW AVERAGE |
| CONDITIONS: | NONE |
| IDEAL WEIGHT RANGE: | 126 TO 162 LBS. |

FIG. 4

DINE ANALYSIS
AND
CONSENSU GUIDELINES

| | | | ACTUAL DIET | CONSENSUS GUIDELINES | |
|---|---|---|---|---|---|
| | TOTAL CALORIES | | 1304 | 1436-1588 | 0.00 |
| MACRO-COMPONENTS | PROTEIN | (CAL) | 162 | 151-227 | +1.00 |
| | SATURATED FAT | (CAL) | 65 | 151 OR LESS | +1.00 |
| | MONOUNSAT FAT | (CAL) | 105 | 151 OR LESS | +0.50 |
| | POLYUNSAT FAT | (CAL) | 124 | 151 OR LESS | +0.50 |
| | COMPLEX CARB | (CAL) | 605 | 680-1210 | 0.00 |
| | DIETARY FIBER | (G) | 20 | 20-35 | +0.50 |
| | SUGAR | (CAL) | 223 | 151 OR LESS | 0.00 |
| MICRO-COMPONENTS | CHOLESTEROL | (MG) | 26 | 300 OR LESS | +1.00 |
| | SODIUM | (MG) | 1489 | 500-3300 | +0.50 |
| | POTASSIUM | (MG) | 1739 | 200-5625 | 0.00 |
| | VITAMIN A | (RE) | 273 | 800 OR MORE | 0.00 |
| | VITAMIN C | (MG) | 30 | 60 OR MORE | 0.00 |
| | IRON | (MG) | 12 | 15 OR MORE | 0.00 |
| | CALCIUM | (MG) | 167 | 800 OR MORE | 0.00 |
| | PHOSPHORUS | (MG) | 731 | 800 OR MORE | 0.00 |

DINE SCORE: 5.00 FAIR

FIG. 5

NUTRIENT BALANCE
MEALS/SNACK BALANCE (FOR EXAMPLE)

| | ACTUAL DIET | CONSENSUS GUIDELINES |
|---|---|---|
| CALORIES | % OF TOTAL CALORIES | |
| PROTEIN | 12% | 10% TO 15% |
| TOTAL FAT | 23% | 30% OR LESS |
|   SATURATED FAT | 5% | 7% OR LESS |
|   MONOUNSAT FAT | 8% | 10% OR LESS |
|   POLYUNSAT FAT | 10% | 10% OR LESS |
| COMPLEX CARB | 46% | 45% TO 80% |
| ADDED SUGAR | 17% | 10% OR LESS |
| ALCOHOL | 0% | 6% OR LESS |
| PROTEIN | % OF PROTEIN CALORIES | |
| PLANT PROTEIN | 55% | 50% OR MORE |
| ANIMAL PROTEIN | 45% | 50% OR LESS |
| FAT | % OF FAT CALORIES | |
| PLANT FAT | 99% | 50% OR MORE |
| ANIMAL FAT | 2% | 30% OR MORE |
| FISH FAT | 0% | 20% OR LESS |
| MEALS | % OF CALORIES BY MEAL | |
| BREAKFAST | 14% | 25% TO 35% |
| LUNCH | 44% | 25% TO 30% |
| DINNER | 42% | 25% TO 35% |
| SNACK | 0% | 8% TO 12% |
| OTHER NUTRIENTS | | |
| ASPARTAME | 0 MG | 2640 MG OR LESS |
| CAFFEINE | 183 MG | 400 MG OR LESS |
| RATIOS | | |
| POL/SAT RATIO | 1.91 | 1.00 OR MORE |
| SODM/POTM RATIO | 0.86 | 1.00 OR LESS |
| CALC/PHOS RATIO | 0.23 | 1.00 OR LESS |

FIG. 6

DINE SCORING SYSTEM

| THE LARGE NUTRIENTS | POINTS | THE SMALL NUTRIENTS | POINTS |
|---|---|---|---|
| 1. ENERGY | +1 | 7. CHOLESTEROL | +1 |
| 2. PROTEIN | +1 | 8. SODIUM | +.5 |
| 3. SATURATED FAT | +1 |     POTASSIUM | +.5 |
| 4. UNSATURATED FATS | | 9. VITAMINS | |
|   A. MONOUNSATURATED | +.5 |   A. VITAMIN A | +.5 |
|   B. POLYUNSATURATED | +.5 |   B. VITAMIN C | +.5 |
| 5. COMPLEX CARBOHYDRATES | +.5 | 10. MINERALS | |
|   A. DIETARY FIBER | +.5 |   A. IRON | +.5 |
| 6. SUGAR | +1 |   B. CALCIUM | +.25 |
| | |   C. PHOSPHORUS | +.25 |
| TOTAL | 6 | TOTAL | 4 |

FIG. 7

CRITERIA FOR SUBTRACTING POINTS FROM THE DINE PROCESS:

| LARGE NUTRIENTS | POINTS | INTAKE |
|---|---|---|
| CALORIES | −1 POINT | LESS THAN 1000 CALORIES OR 50% OR MORE OVER IDEAL CALORIC LEVEL (ICL) |
| PROTEIN | −1 POINT | LESS THAN 6% ICL OR MORE THAN 30% ICL |
| TOTAL FAT | −1 POINT | MORE THAN 45% ICL |
| COMP CARB | −.5 POINT | LESS THAN 25% ICL OR MORE THAN 80% ICL |
| FIBER | −.5 POINT | LESS THAN 12 GM |
| SUGAR | −1 POINT | MORE THAN 20% ICL |

FIG. 8

METHOD FOR EVALUATING AND ANALYZING FOOD CHOICES

REFERENCE TO RELATED APPLICATIONS

This application is a continuation in part of application No. 07/671,146 entitled DINE Process Evaluation for Analyzing Food Choices, now abandoned, filed Aug. 27, 1991.

FIELD OF THE INVENTION

This invention relates generally to the evaluation of an individual's food choices based upon selected factors which will lead to healthier choices of foods for an individual.

BACKGROUND OF THE INVENTION

Six of the ten leading causes of death in the United States are heart disease, certain cancers, stroke, cirrhosis of the liver, diabetes mellitus and atherosclerosis. Each of these disorders has been shown to have a nutrition related component. Contributing to the prevalence of diet-related disorders is the lack of a single, standardized process by which the public can objectively evaluate all aspects of the food choices which affects its eating patterns. At the present time there is no easy method by which the public can evaluate "how well" or "how poorly" it is eating.

The government has provided systems for evaluation of certain aspects of diet. For example the Recommended Dietary Allowances published by the United States Department of Agriculture (RDA 1989) provides nutrient allowances for good health. The RDA does not however provide an easy method for individuals to use in determining if their diets are adequate in these various nutrients. A professional nutritionist is required to complete a diet analysis and then interpret the data for the individual. This analysis involves reviewing the amount of nutrients obtained in various aspects of the diet and comparing the summation of those nutrients to the RDA. The Dietary Goals for the United States (1977) and the Dietary Guidelines for Americans (1990) explain how much of various nutrients an individual should consume and recommend the number of servings of food to eat to obtain the required nutrients. However, these goals and guidelines again do not provide the means for an individual to know if particular food choices give the appropriate amount of nutrients.

In summary, the three dietary recommendation sources cited above do not provide an individualized process for evaluating food choices. Further they require the help of a skilled professional to interpret the results. In general, an individual, unless trained, cannot comprehensively evaluate his diet based on these dietary recommendation sources.

In contrast to the above the present invention can assist an individual in evaluating food choices. Further, it incorporates the dietary recommendations and principles cited in the above methods so that an individual can evaluate food choices and how well the individual's diet is meeting the various federal/national recommendations.

SUMMARY OF THE INVENTION

The present invention allows an individual to evaluate the food choices made by that person and allows a determination of how well or how poorly that person is eating. The present invention also allows an individual to determine the weak and strong points in that person's diet thereby allowing the individual to make appropriate changes in food choices.

It has been estimated that there are ninety-two different nutrients/components which are related to human nutrition. In some cases certain of these nutrients/components are required in large amounts and others in much smaller amounts. For other classes of nutrients/components there is only speculation as to whether there is a specific need for the nutrient in human nutrition. The present invention selects fifteen of these nutrients/components which have been determined through statistical procedures and surveys of nutritional scientists to be vital to human nutrition and important to human health. These fifteen nutrients/components are defined as "predictor nutrients." It has also been determined that certain other nutrients or "follower nutrients/components" would also generally be adequate in a diet when the predictor nutrients in the diet are consumed within appropriate guidelines.

Thus for various studies, it has been determined that it is not necessary to monitor all ninety-two nutrients when in fact foods which contain adequate supplies of predictor nutrients will also contain adequate supplies of various follower nutrients.

As an example of this concept if an individual consumes food which contains a sufficient amount of complex carbohydrates and protein to meet various guidelines such foods would also most likely fulfill the Recommended Dietary Allowances for B Vitamins. Therefore B vitamins are not designated as predictor nutrients but as follower nutrients in the present invention. Thus by including appropriate predictor nutrients in a diet in recommended amounts, various other follower nutrients which are also required can also be obtained.

In the present invention fifteen predictor nutrients have been determined and are used to quantify an individual's food choices. These fifteen predictor nutrients are organized into ten categories. Each category represents a quantifiable area for evaluation of food choices. Thus by identifying the foods eaten in certain categories observations can be made which will improve the food choices made by an individual.

The present invention uses a scoring system and descriptors to measure the nutritional status and progress achieved by individuals. This information is subsequently used in a decision making process to improve the food choices made by the individual. The present invention utilizes a scoring system to identify the weekly food choice goals and to structure subsequent food choice actions by the individual to achieve these goals. The system also provides positive messages when the goals have been achieved and negative messages when the individual diet is evaluated to be outside of acceptable ranges. The score that is reported to the user is as follows: 10-perfect; 9 to 8-excellent; 7 to 6-good; 5 to 4-fair; 3 to 2-poor; 1 to 0-very poor.

BRIEF DESCRIPTION OF THE DRAWINGS

FIG. 1 A table of predictor and follower nutrients
FIG. 2 The DINE Process relational schema
FIG. 3 Sample food record
FIG. 4 Individual record
FIG. 5 DINE Dietary/Activity analysis and consensus guidelines
FIG. 6 Nutrient balance, meals/snack balance
FIG. 7 The DINE scoring system FIG. 8 Criteria for subtracting points from the DINE Process FIGS. 9-19 The Process flow chart

DETAILED DESCRIPTION OF THE PREFERRED EMBODIMENT

Referring to FIG. 1 the predictor and follower nutrients of the present invention are disclosed. For example when a predictor nutrient such as protein is consumed various follower nutrients such as vitamins B1, B2, B6, B12, D and K are also simultaneously consumed. In addition other minerals such as copper, chromium etc. are also consumed along with protein. When a predictor nutrient/component such as dietary fiber is consumed, various follower nutrients such as B vitamins, and complex carbohydrates are also consumed. Further, when a predictor nutrient such as vitamin A is consumed, in general, fiber, vitamin C, and potassium are also consumed. These predictor and follower nutrients/components form the basis of the present invention.

Figure 2:
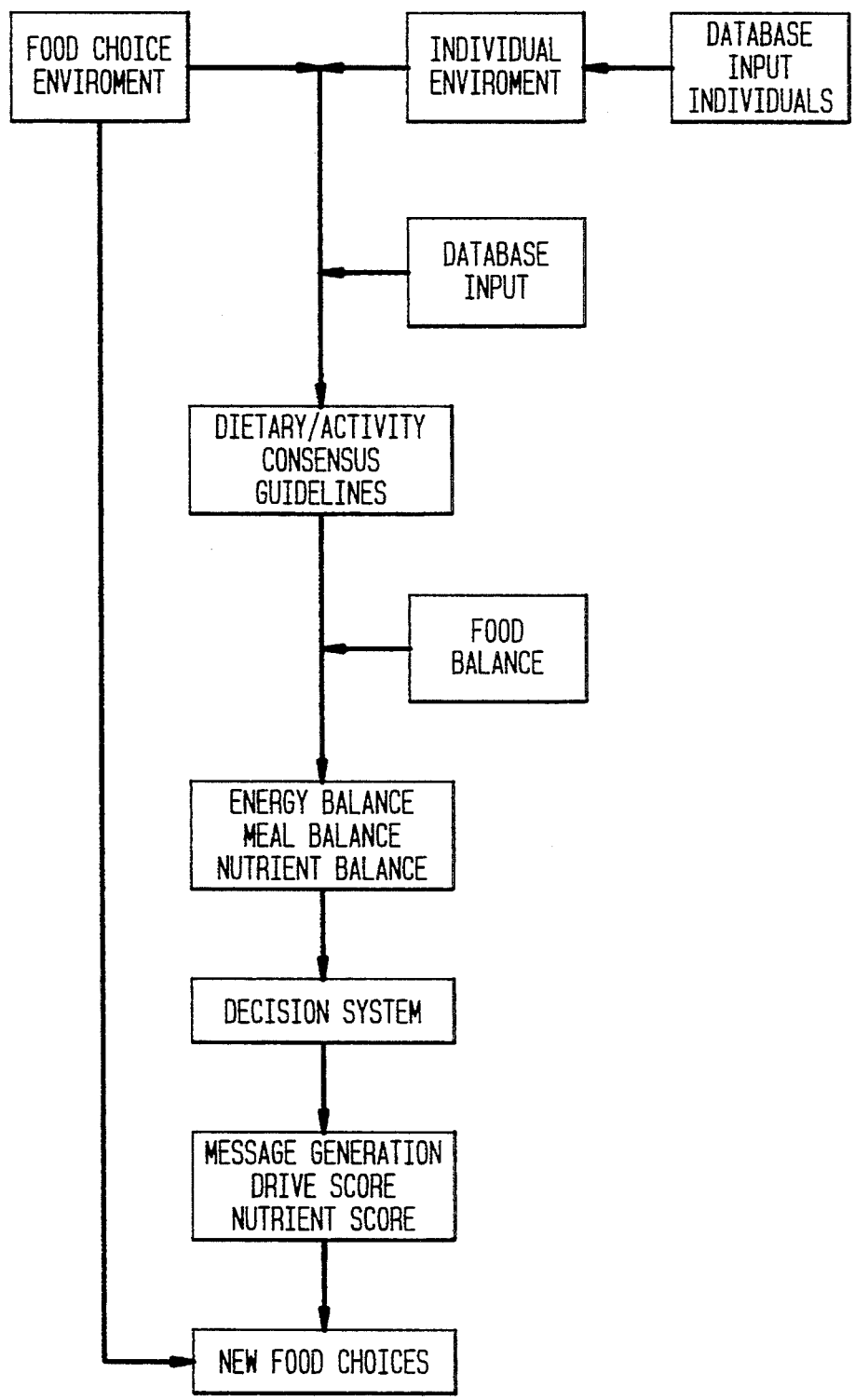

Referring to FIG. 2 the DINE Process relational schema is described. An individual has a particular food choice environment [20] which are the foods and beverages consumed in a daily diet, that is, the food consumed by an individual during the day. In addition the individual has an individual environment comprising that person's physical makeup and biomedical background [22]. These two categories of data, the food choice environment and the individual environment combine to create a dietary/activity recommendation [30] which also incorporates the various consensus dietary guidelines [24]. These guidelines together with the additional information relating to the individual combine to create recommendations for meals, snacks, and nutrient balance [26]. This information in turn is used by the invention in a decision system [28] which takes into account the individual characteristics and the food consumed to create a series of messages [30] which are presented to a user and which advise the user that the person is high or low or within an appropriate range in certain nutrients and the recommendation for the appropriate food choices to overcome nutrient/component imbalance.

As part of the output from an evaluation a series of messages are output to the user providing details of the evaluation with respect to specific nutrients. Those messages are as follows

TOTAL CALORIES

Calories—Your calorie intake was over your ideal caloric range. Eating consistently above your energy needs leads to overweight and obesity and consequently to many nutrition related diseases.

Calories—Your calorie intake was below your ideal caloric range. Undereating may make you more susceptible to health problems including lowered resistance to infectious disease and headaches. A low intake may cause you to feel tired and may also lead to binge eating due to ravenous hunger.

Calories—Your calorie intake was within your ideal caloric range. You are succeeding in meeting your body's energy needs. Maintaining an intake within your ideal caloric range provides your body with energy for a healthy, active lifestyle and helps maintain optimal body weight.

PROTEIN

Protein—Your protein intake accounted for more than 15% of your ideal caloric level. Too much protein strains your kidneys and may cause you to lose calcium. Protein consumed in excess of the amount you need is converted to and stored in your body as fat. High protein foods include beef, pork, poultry, fish nuts, dried beans and dairy products. Foods generally lower in protein are fruits, vegetables and grains.

Protein—Your protein intake accounted for less than 10% of your ideal caloric level. Protein is necessary for maintaining body tissues, proper wound healing and resistance to disease. 10% to 15% of your daily caloric intake should come from protein. Good sources of protein are lean meat, poultry, fish, nuts, dried beans and lowfat dairy products. Fruits, vegetables and grains are generally lower in protein.

Protein—Your protein intake was right on target. Adequate protein provides the building blocks for the repair and maintenance of body tissues, proper wound healing and disease resistance. Continue to choose sources of protein that are also low in fat such as lean meat, poultry, fish, dried beans and lowfat dairy products. Fruits, vegetables and grains are generally lower in protein.

CARBOHYDRATES

Carbohydrates—Your complex carbohydrate intake accounted for more than 80% of your ideal caloric level. Excess carbohydrate intake makes it difficult to achieve a proper balance of protein and fats as well as other nutrients. Foods high in complex carbohydrates include breads, cereals, grains, pastas, fruits, vegetables and dried beans.

Carbohydrates—Your complex carbohydrate intake accounted for less than 45% of your ideal caloric level. A low complex carbohydrate intake also decreases your likelihood of obtaining enough fiber in your diet. Foods high in complex carbohydrates include breads, cereals, grains, pastas, fruits, vegetables and dried beans.

Carbohydrates—Your complex carbohydrate intake was within 45%-80% of your ideal caloric level. Consuming carbohydrates at this level makes it easier for your body to function with the energy, vitamins and minerals it needs for good performance. Foods high in complex carbohydrates include breads, cereals, grains, pastas, fruits, vegetables and dried beans.

FIBER

Fiber—Your fiber intake was greater than recommended. A diet that is too high in fiber may cause poor absorption of vitamins and minerals and lead to nutritional deficiencies. Too much fiber may also cause intestinal discomfort, bloating, diarrhea and cramping. Foods high in fiber are whole grain breads and cereals, dried beans and peas, and many fruits and vegetables.

Fiber—Your fiber intake was less than recommended. The recommended daily intake for fiber is 20-35 grams. A low fiber intake is associated with constipation and other digestive problems. There is also evidence that a low fiber intake contributes to some forms of cancer. Foods high in fiber are whole grain breads and cereals, dried beans and peas, and many fruits and vegetables.

Fiber—Your fiber intake was within the recommended range of 20-35 grams per day. Your diet is providing the right amount of fiber to maintain proper digestion and good health. Continue to select foods high in fiber such as whole grain breads and cereals, dried beans and peas, and many fruits and vegetables.

SODIUM
- Sodium—Your sodium intake was greater than recommended. A diet too high in sodium can cause water retention and lead to high blood pressure. Processed foods such as frozen dinners, canned vegetables, and luncheon meats are high in sodium.
- Sodium—Your sodium intake was less than recommended. Sodium is necessary for proper water balance and the transmission of nerve impulses in the body. The small quantity of sodium needed daily can be obtained from the sodium which naturally occurs in foods. The main source of sodium is salt.
- Sodium—Your sodium intake was within the range of adequate intake. Sodium is important for proper water balance and nerve transmission but too much can cause water retention and lead to high blood pressure. Selecting unprocessed fruits, vegetables and whole grains, and avoiding processed foods such as frozen dinners, cured meats and canned goods will help you keep your sodium intake within the recommended range.

POTASSIUM
- Potassium—Your potassium intake was greater than the recommended range. A continuously high intake of potassium can eventually lead to kidney failure, severe dehydration and weakening of the heart muscle. Foods high in potassium include legumes, whole grains, oranges, bananas, leafy vegetables, broccoli, potatoes, and meats.
- Potassium—Your potassium intake was less than recommended. Potassium is needed to regulate heartbeat and maintain fluid balance and blood pressure. Foods high in potassium include legumes, whole grains, oranges, bananas, leafy vegetables, broccoli, potatoes, and meats. Most mixed dishes are also high in potassium.
- Potassium—Your potassium intake was within the recommended range. An adequate potassium intake helps maintain body water balance and helps to insure proper nerve impulse transmission. A varied selection of foods such as legumes, whole grains, oranges, bananas, leafy vegetables, broccoli, potatoes, and meats will provide the recommended amount of potassium.

TOTAL FAT
- Total fat—Your total fat intake was more than 30% of your ideal caloric level. A high fat intake is associated with overweight, obesity heart disease and other nutrition related diseases. Foods high in fat include margarine, butter, oils, most cheeses, whole milk dairy products, untrimmed meats and poultry, fried foods, gravies, sauces, bacon and luncheon meats. To reduce fat, trim meats, skin poultry, choose cooking methods that add little or no fat (such as broiling or stir-frying), choose reduced fat cheeses, margarines, and dairy products and use less oil in cooking.
- Total fat—Your total fat intake was within the recommended range (less than 30% of your ICL). A moderate intake of fat helps insure maintenance of body weight, decreases your risk for heart disease, and provides satiety and flavor to your diet.

SATURATED FAT
- Saturated fat—Your intake of saturated fat was greater than 10% of your ideal caloric level. A high intake of saturated fat increases your risk of heart disease and possibly some forms of cancer. Foods high in saturated fat include meats, eggs, whole milk dairy products, and tropical oils (coconut, palm and palm kernel).
- Saturated fat—Your intake of saturated fat was within the recommended range. A diet low in saturated fat decreases your risk of heart disease and possibly some forms of cancer. Foods lower in saturated fat include lowfat or nonfat dairy products, egg substitutes, nuts and legumes, and corn, sunflower, and safflower oils.

MONOUNSATURATED FAT
- Monounsaturated Fat—Your intake of monounsaturated fat greater than 10% of your ideal caloric level. While not specifically associated with any one disease, overeating foods that contain this type of fat contributes to an overall high fat intake and consequently a higher risk of over weight, obesity, heart disease, and other nutrition related diseases. Foods high in monounsaturated fat include olives and olive oil, avocados, and mayonnaise.
- Monounsaturated Fat—Your intake of monounsaturated fat was within the recommended range. This level may provide protection against heart disease. Foods high in monounsaturated fat include olives and olive oil, avocados, and mayonnaise.

POLYUNSATURATED FAT
- Polyunsaturated Fat—Your intake of polyunsaturated fat was greater than 10% of your ideal caloric level. A diet too high in polyunsaturated fat is likely to be high in total fat and may contribute to some forms of cancer. Foods high in polyunsaturated fats include tub margarine, safflower and sunflower oils, fish, and walnuts.
- Polyunsaturated Fat—Your intake of polyunsaturated fat was within the recommended range. This level may provide protection against heart disease and possibly some forms of cancer. Foods high in polyunsaturated fat include tub margarine, safflower and sunflower oils, fish, and walnuts.

CHOLESTEROL
- Cholesterol—Your cholesterol intake was greater than the recommended level. Too much dietary cholesterol increases your risk of heart disease. Foods high in cholesterol include eggs, beef, unskinned poultry, and whole milk dairy products.
- Cholesterol—Your cholesterol intake was within the recommended range. A low fat, low cholesterol diet lowers your risk of heart disease and other nutrition related diseases. Foods with little or no cholesterol include lowfat dairy products, legumes, grains, fruits and vegetables.

SUGAR
- Sugar—Your sugar intake accounted for more than 10% of your ideal caloric level. Sugar contributes only calories to your diet and provides no other nutrients. An excess sugar intake contributes to dental caries, overweight, obesity, and diabetes. It also takes the place of foods that would otherwise be contributing nutrients. High sugar foods include regular soft drinks, candy, desserts, cookies, cakes, frozen desserts such as ice cream or ice milk, and flavored yogurts.

ALCOHOL
- Alcohol—Your intake of alcohol exceeded the recommended level. Consuming alcohol beyond this level makes it difficult to obtain the proper balance of nutrients and additionally creates other potential health problems related to the concentration of alcohol in the blood. Choose non-alcoholic mixed drinks, lower alcohol beers or drink fewer alcoholic beverages.

Alcohol—Your intake of alcohol did not exceed the recommended level. This level of intake insures that alcohol is not displacing other more valuable nutrients in your diet.

CAFFEINE

Caffeine—Your intake of caffeine was higher than the maximum level advised. Excess caffeine intake contributes nervousness, irritability and increased gastric production. It is also a diuretic and may contribute to dehydration. Foods high in caffeine include coffee, tea, colas, and chocolate.

Caffeine—Your intake of caffeine was within an acceptable range. Caffeine is a substance unnecessary for good health and may actually be detrimental in larger quantities. To keep your intake of caffeine low, avoid coffee, tea, colas, and chocolate.

VITAMIN A

Vitamin A—Your vitamin A intake was less than recommended. Too little vitamin A may lead to night blindness and irritation of the mucous membranes. Skin problems may also result. Low vitamin A intake may possibly be a factor in the development of cancer. Rich sources of vitamin A include liver, carrots, spinach, broccoli, winter squash and other dark green leafy vegetables.

Vitamin A—Your vitamin A intake was within the guidelines for a healthy diet. A proper intake insures proper night vision, healthy skin and mucous membranes. Vitamin A may decrease your risk of some forms of cancer. Selecting a variety of vegetables such as carrots, spinach, broccoli, winter squash and other dark green leafy vegetables will supply adequate amounts of vitamin A.

VITAMIN C

Vitamin C—Your diet was low in vitamin C. An adequate daily supply of vitamin C is necessary for resistance to infection and proper wound healing. Vitamin C also aids in the absorption of iron and other minerals. Cigarette smokers require twice as much of this vitamin as nonsmokers. Foods high in vitamin C include oranges, grapefruit, kiwi fruit, broccoli and cabbage.

Vitamin C—Your intake of vitamin C was within the guidelines for good health. An adequate intake of vitamin C helps increase resistance to infection, improves wound healing and maintains mucous membrane integrity. Choosing a variety of fruits and vegetables such as oranges, grapefruit, kiwi fruit, broccoli, cabbage and lemons will help insure adequate intake of vitamin C.

IRON

Iron—Your iron intake was less than recommended. Iron is needed to transport oxygen to maintain healthy body tissues. A low intake can lead to anemia and fatigue. Foods high in iron include red meats, mustard greens, kale, and fortified breads and cereals.

Iron—Your diet provided the recommended amount of iron necessary for good health. Iron moves oxygen through the blood to the tissues for their maintenance. An adequate intake helps prevent anemia and fatigue. Selecting lean red meats, mustard greens, kale, and fortified breads and cereals will continue to provide you with adequate iron for a healthy diet.

CALCIUM

Calcium—Your intake of calcium was low. Calcium is essential for proper bone growth and development. It is also important in muscle contraction and the transmission of nerve impulses. Good sources of calcium include lowfat and nonfat dairy products, broccoli, mustard greens, and kale.

Calcium—Your diet is providing the amount of calcium you need for proper bone growth and development. A diet adequate in calcium is also important in muscle contraction and the transmission of nerve impulses. Continue to include lowfat and nonfat dairy products, broccoli, mustard greens, and kale in your daily diet.

PHOSPHORUS

Phosphorus—Your diet was low in phosphorus. Phosphorus is essential in the breakdown of food for energy and is an important component of bones and teeth. Foods high in phosphorus include meats, dairy products and baked products.

Phosphorus—Your diet provides adequate phosphorus for healthy bones and teeth. Phosphorus also functions in the breakdown of food for energy. Good sources of phosphorus include lean meats, lowfat dairy products and lowfat baked products.

In addition to the above messages a score [32] is presented to the individual so the individual knows how well he or she is eating with respect to the food choices. As a result of this score, making new food choices [34] is recommended. New food choices then comprise the food choice environment [20] in which that person is operating. This entire evaluation and cyclical advising of the individual occurs so that the person over time will modify the food choices to achieve the various recommended guidelines.

Referring to FIG. 3 a FOOD CHOICE ENVIRONMENT is described. For example, in the sample shown the individual had danish pastry, coffee, with coffee whitener and sugar for breakfast. For dinner, the individual consumed, among other things, pasta, sauce, squash, etc. This food choice environment makes up that block of information in FIG. 2.

Referring to FIG. 4 an Individual Environment is described. For example the sample person in FIG. 4 is a female age 36 years having certain other characteristics.

Referring to FIG. 5 a DINE Dietary analysis and consensus guidelines are developed for the particular individual described in FIG. 4. Those recommendations include recommendations for large and small nutrients, what has actually been consumed by the individual and consensus guidelines for the individual. A score is also given so that a person can determine whether the person's diet is within the appropriate guidelines.

Referring to FIG. 6 the nutrient balance for meals and snacks is described. The actual diet is calculated in terms of the appropriate percent of, for example, protein consumed and whether it falls within the appropriate consensus guideline. It should be noted that as nutrient guidelines change, modifications can be made to the present invention to adjust points and nutrient/component changes, additions and subtractions.

Referring to FIG. 7 the DINE SCORING SYSTEM is described. This score represents a comparison between an individual's values and consensus values. If an individual is eating with the appropriate consensus guidelines one point per category is awarded for such behavior for up to a maximum of ten points. Each category comprises between one and three nutrients. These categories have been selected based upon the statistical analysis described earlier. Thus in those cases where one category comprises one nutrient, the behavior of eating appropriate amounts of such nutrient is awarded one point. In the case of a category where two nutrients are present, each nutrient which is consumed in an appropriate amount is awarded one-half point. In the case of three nutrients per category, one nutrient is worth one half point and other nutrients are worth one quarter point each. Thus in FIG. 7 large single nutrient categories such as protein and saturated fats are each worth one point. In a category where both monounsaturated and polyunsaturated fats are present each nutrient is worth a half point. In the small nutrient category, category 8 comprising sodium and potassium are each worth a maximum of one 4 half point and category ten comprising three different minerals (iron, calcium, and phosphorus) are worth one half point for iron, one quarter point for calcium and one quarter point for phosphorus.

If the intake of a particular nutrient is not within the recommended guideline a zero or no point score is given. If the nutrient is unhealthfully outside the guideline a minus is given which subtracts one point from the score.

Referring to FIG. 8 the various criteria for subtracting points from the DINE score are listed. Thus if calories are added at an unhealthful level either above or below the recommended level one point is subtracted. If protein is consumed in amounts above or below the recommended level one point is deducted and so on.

A score of ten (perfect) indicates that food choices consumed by the individual were within each of the guidelines for the selected nutrients. A score of zero indicates that none of the guidelines were achieved. Other categories of performance are as follows: 8-9 excellent, 6-7 good, 4-5 fair, 2-3 poor and 0-1 very poor. Thus under this process a score from zero to ten reflects the quality of an individual's diet. The actual nutrients taken in by an individual through diet are compared with dietary guidelines that have been specifically calculated for the individual based upon individual medical and biological information. The objective of the individual is to achieve a score of eight or more points to reflect "excellent" food consumption and compliance with dietary guidelines.

Figure 9:
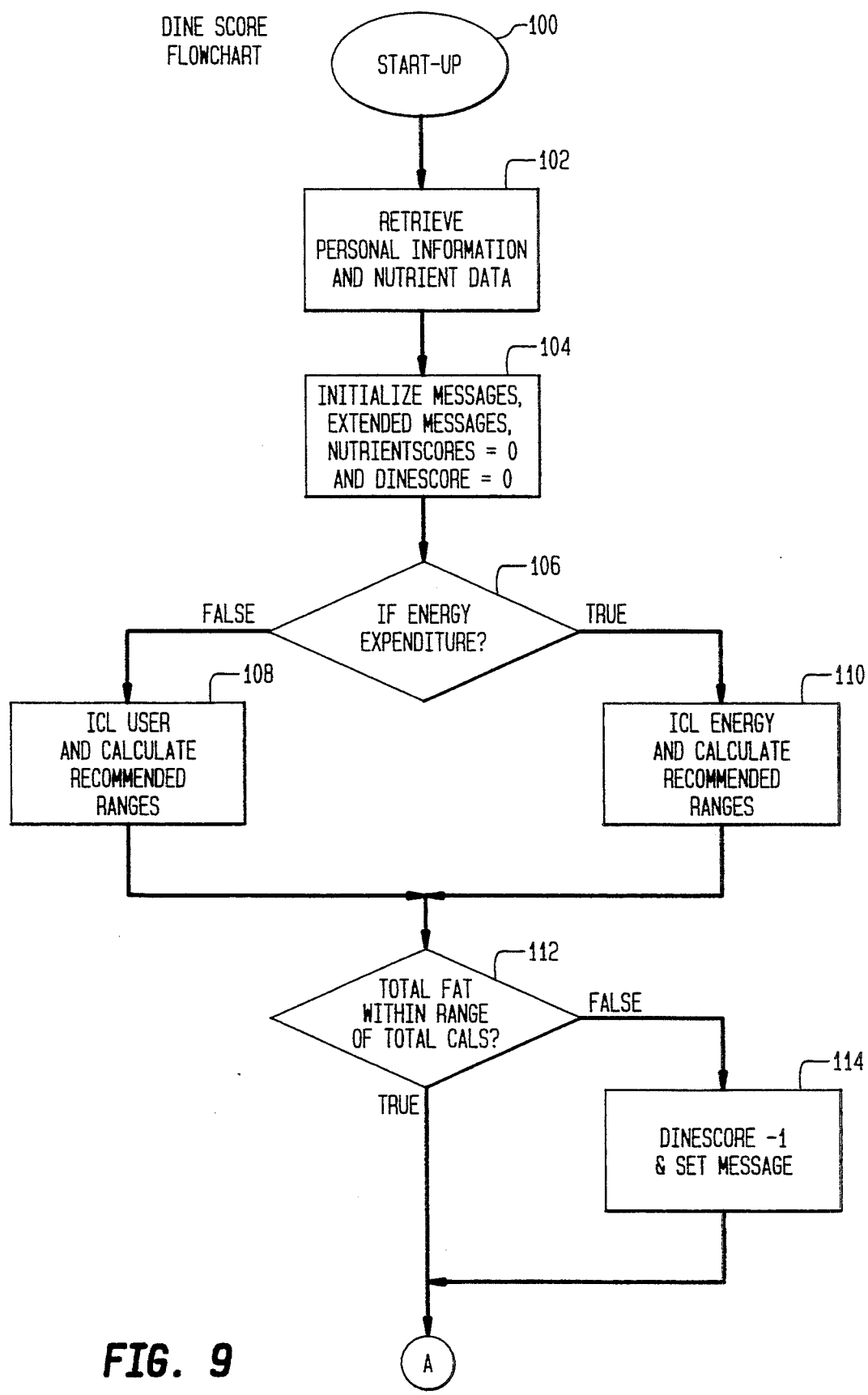

Referring to FIG. 9 the start-up of the evaluation process is described. The software application program is started by the user [100]. The program is written in any programming language compatible with the computer system used, to implement the scheme shown by the flow diagrams and described in this specification. The program initially retrieves personal information and nutrient data that relates to the individual who is running the program [102]. The software application program may be run on any type of computer or data processing system. In the preferred embodiment, the software program is used with an IBM compatible personal computer ("PC") equipped with an Intel (Trademark) 80286 microprocessor or equivalent. An alternate embodiment runs on a PC utilizing an Intel (Trademark) 80386 or equivalent (a more powerful microprocessor). Another alternate embodiment comprises a Motorola (Trademark) 68000 series microprocessor based computer, such as an Apple Macintosh. The actual type of computer used is really not important, as long as the computer has enough memory to store and run the program and to store all the necessary user data. The computer must also have some form of output device, such as a display or printer, in order to present messages to the user. The memory will be divided into four sectors. The first memory sector, the data base, will be used to store all information regarding the user's actual dietary intake and individual environment. The second memory sector, the nutrient base, will store the consensus dietary guidelines. The third memory sector, the knowledge base, will store all the parameters of the program used as rules for manipulating the information in the data base to provide the organized historical record of the user's dietary intake and a recommended future diet for the user. This may simply be a look up table, used in conjunction with the microprocessor for performing manipulation on the data base contents under direction of the software application program. The fourth memory sector, the result base, will store this record and recommended future diet so that the software application program can send the result base contents to the output device.

All messages and various scores are initialized to a zero value [104]. The software next determines if energy is being expended in the form of exercise at various levels by the user [106]. If a user is reasonably sedentary the ideal nutrients and recommended ranges for nutrients are determined [108]. If a user is active at different levels a different series of recommended ranges for nutrients is determined [110].

Based upon food information provided by the user and stored in the computer memory data base, the total fat content of diet is determined [112]. If the total amount of fat is outside of the recommended range of total calories DINE score of "−1" is awarded and a series of messages relating to excess fat content and diet are created [114]. If total fat is within appropriate range of total calories the system moves on to determine the total calories consumed.

Figure 10:
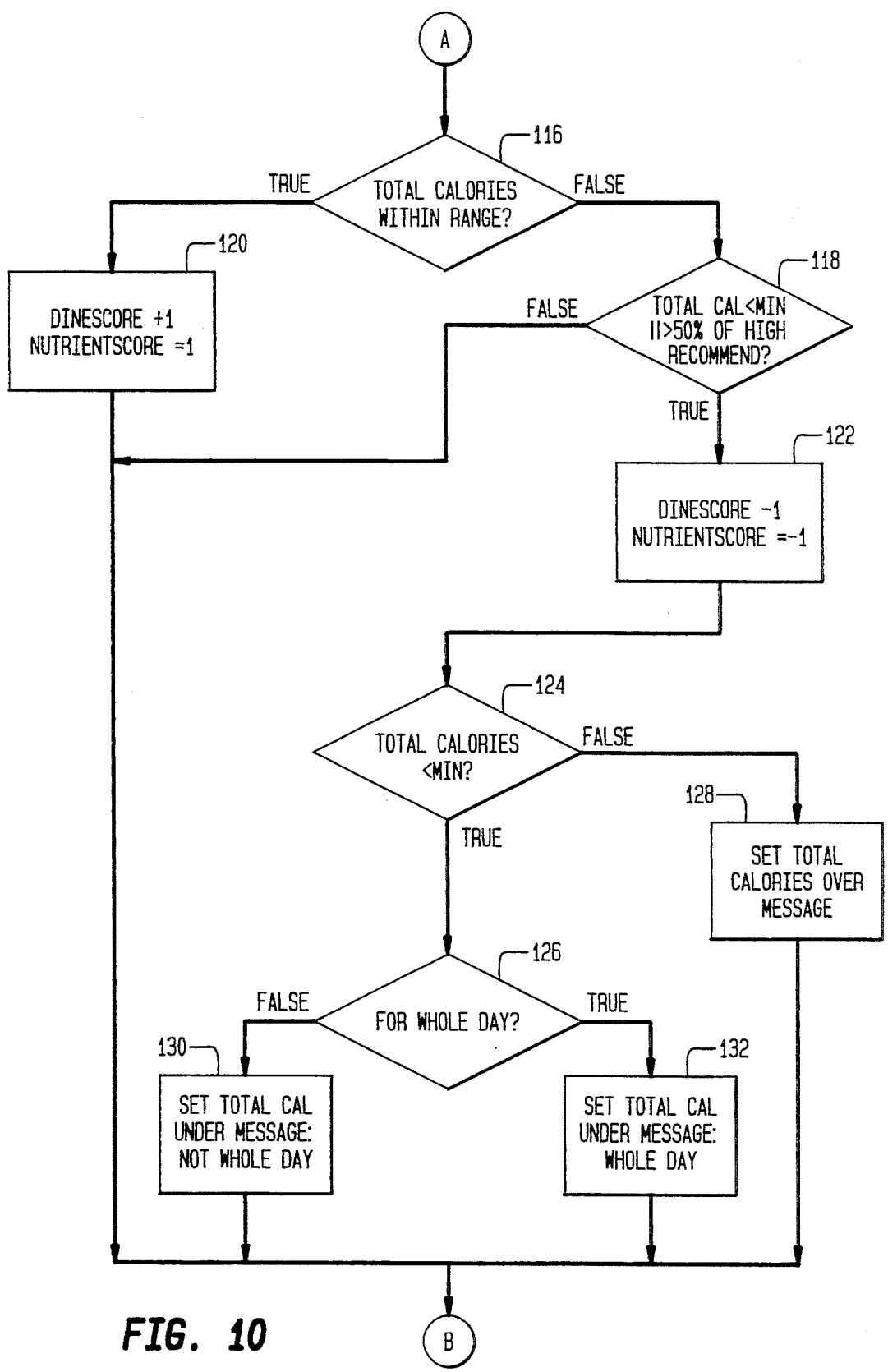

Referring to FIG. 10, the total calories are evaluated to determine if they are within the appropriate range for the individual in question [116]. If the total calorie intake is less than a minimum quantity or more than fifty percent higher than recommended [118] a score of "−1" is given together with a nutrient score of "−1" [122]. If the total calories are less than a prescribed minimum [124] the system inquiries whether the total calorie intake was for an entire day [126]. If the excess calories were consumed for the entire day an appropriate message relating to over consumption of calories is recalled [128]. If the entire day's calories were not yet consumed, a different message is recalled [132]. If the calorie intake is above a certain minimum but it is not for the whole day a calorie message noting that calories have been under consumed for the day is generated [130]. If the total number of calories for a given meal are not greater than the minimum but are still greater than the recommended amount for that meal a message is recalled relating to an excess of calories [128].

Figure 11:
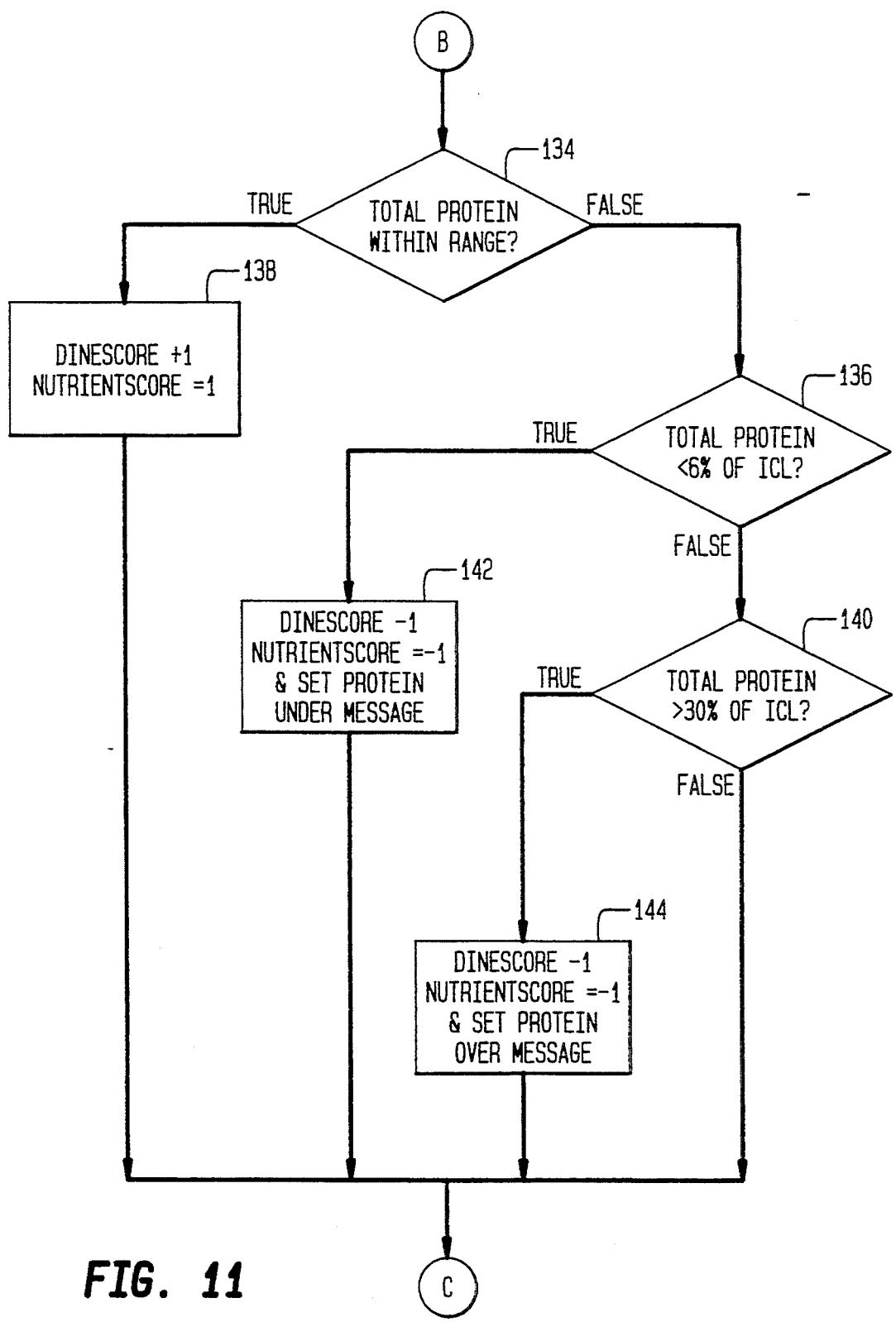

Referring to FIG. 11 the protein content of a diet is next evaluated. The total amount of protein based on the individual's diet is evaluated [134]. If the total protein content is not within 10-15% of the ideal caloric level (ICL) the system next determines if the total protein content is less than six percent of the ICL [136]. If total protein content is less than six percent of ICL negative DINE score of "−1" and a nutrient score of "−1" assigned and an appropriate protein under consumption message is generated [142]. If total protein content is above six percent of ICL the system next evaluates if the total protein content is greater than thirty percent of ICL [140]. If more than thirty percent of ICL is consumed in protein a DINE score of "−1" and a nutrient score of "−1" assigned and a protein over consumption message is generated [144]. Thereafter the system continues with the evaluation. If total protein is not over thirty percent the system moves on to the next stage of the evaluation.

If the total protein consumed is within range [134] a DINE score of "+1" and a nutrient score of "+1" assigned [133] and the system moves to the evaluation of fat consumption.

Figure 12:
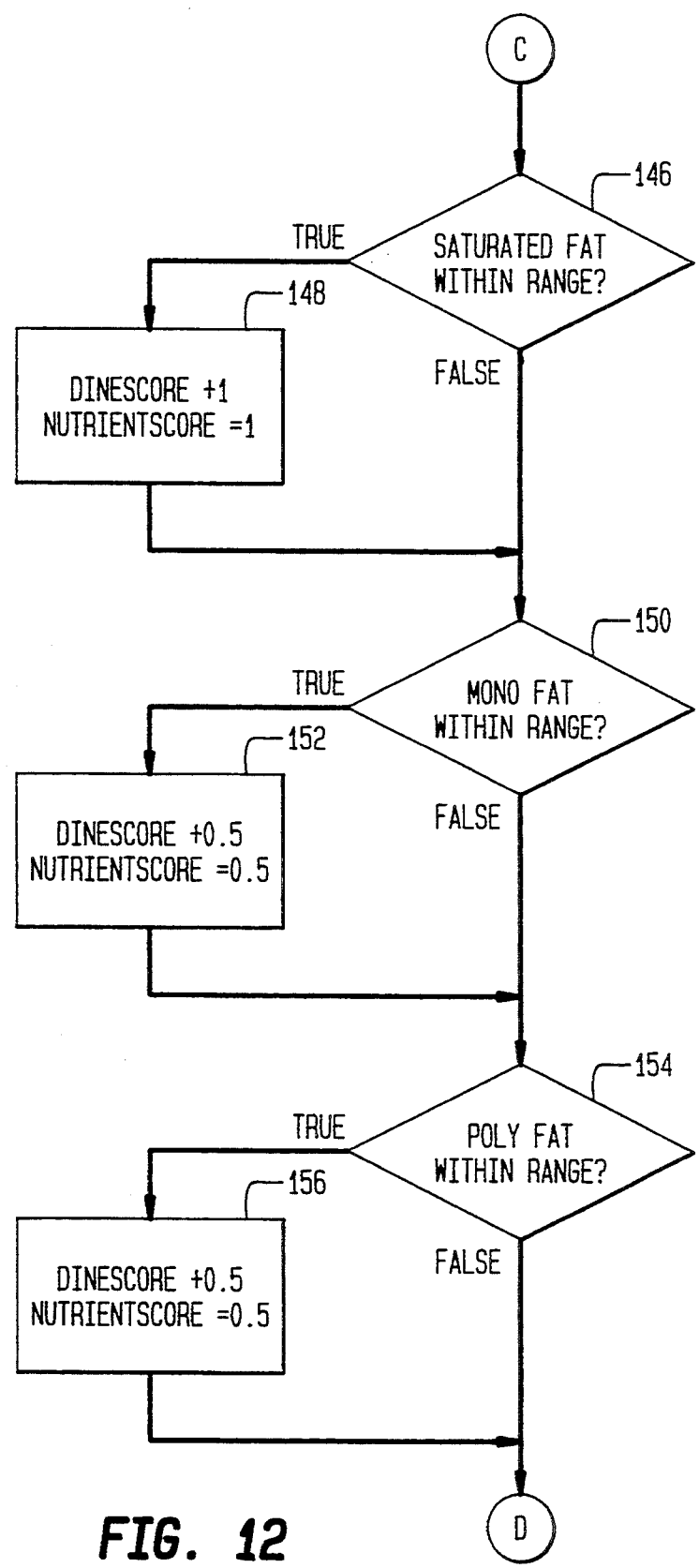

Referring to FIG. 12 the system first determines if the saturated fat is within the appropriate range for the individual [146]. If an appropriate amount of saturated fat is being consumed a DINE score of "+1" and a nutrient score of "+1" are assigned [148]. If the amount of saturated fat is not within range the system next evaluates if the amount of monounsaturated fat is within range [150]. If the amount of monounsaturated fat being consumed is within range a DINE score of "+0.5" and a nutrient score of "+0.5" is assigned [152]. If the amount of monounsaturated fat is not within range an evaluation of the polyunsaturated fat is made to determine if it is within range [154]. If the amount of polyunsaturated fat is within range a DINE score of "+0.5" and a nutrient score of "+0.5" are assigned [156].

Figure 13:
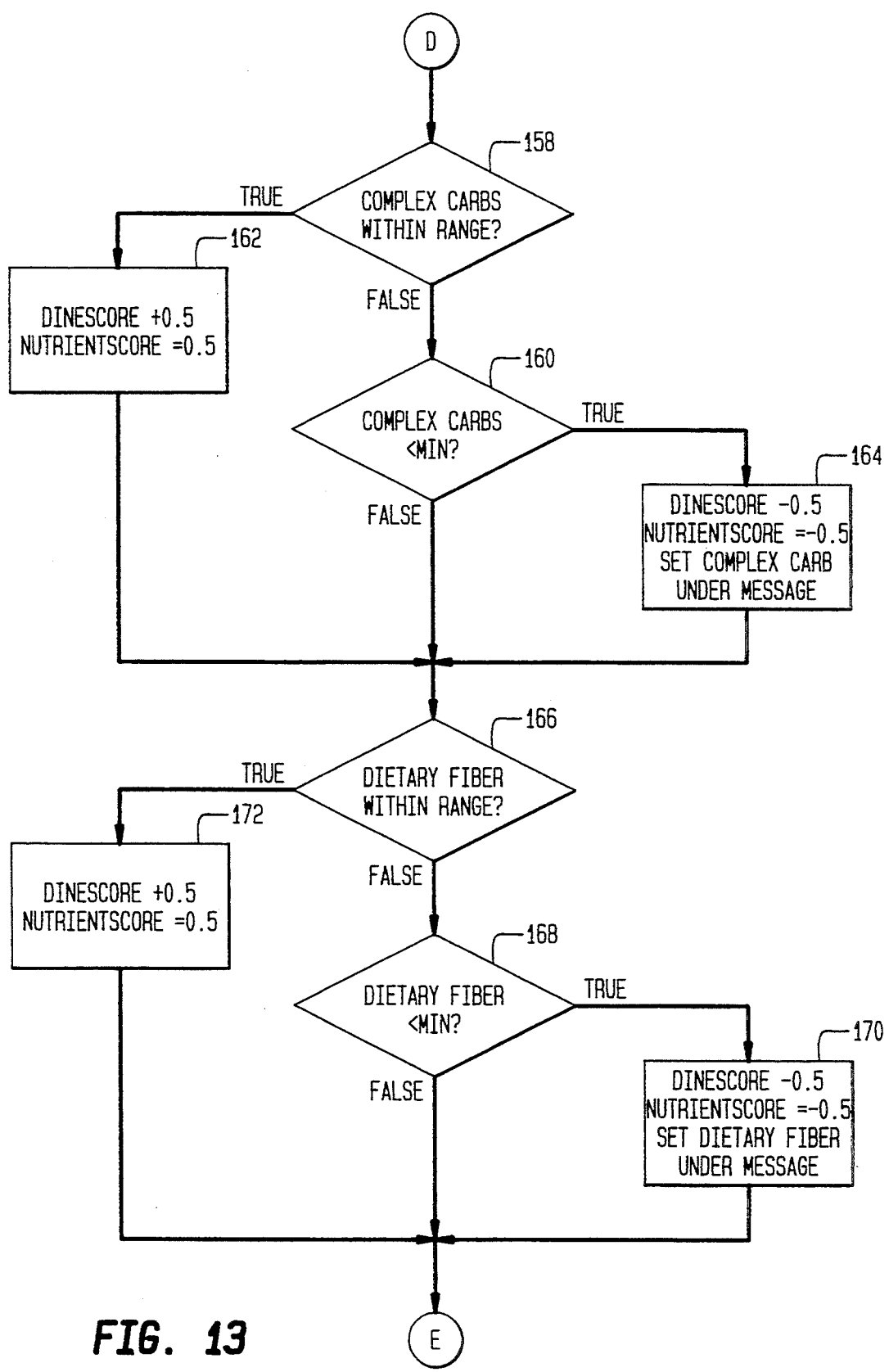

Referring to FIG. 13 complex carbohydrate and fiber are evaluated. The system determines if the amount of complex carbohydrates consumed are within an appropriate range [158]. If they are not, the system next determines if the amount of complex carbohydrates is less than an appropriate minimum for the individual [160]. If the amount consumed is less than recommended a DINE score of "−0.5" and a nutrient score of "−0.5" are assigned and appropriate message regarding under consumption of complex carbohydrates is generated [164]. If the amount of complex carbohydrates consumed is greater than the minimum amount the system then continues on to the next evaluation. If the amount of complex carbohydrates is within an appropriate range a DINE score of "+0.5" and a nutrient score of "+0.5" are assigned [162] and the system continues to the next evaluation.

The system next evaluates the amount of dietary fiber consumed. The system first determines if that dietary fiber consumption is within an appropriate range [166]. If the amount consumed is not within range the system next determines if the amount of dietary fiber consumed is below a minimum recommended amount for the individual [168]. If less than a minimum amount is consumed a DINE score of "−0.5" and a nutrient score of "−0.5" are assigned and an appropriate under consumption of dietary fiber message is generated [170]. If the amount of dietary fiber consumed is greater than a minimum the system proceeds to the next evaluation phase.

If the amount of dietary fiber consumed is within range a DINE score of "+0.5" and a nutrient score of "+0.5" are assigned together with a nutrient score equal to "+0.5" [172] and the system proceeds with the next evaluation.

Figure 14:
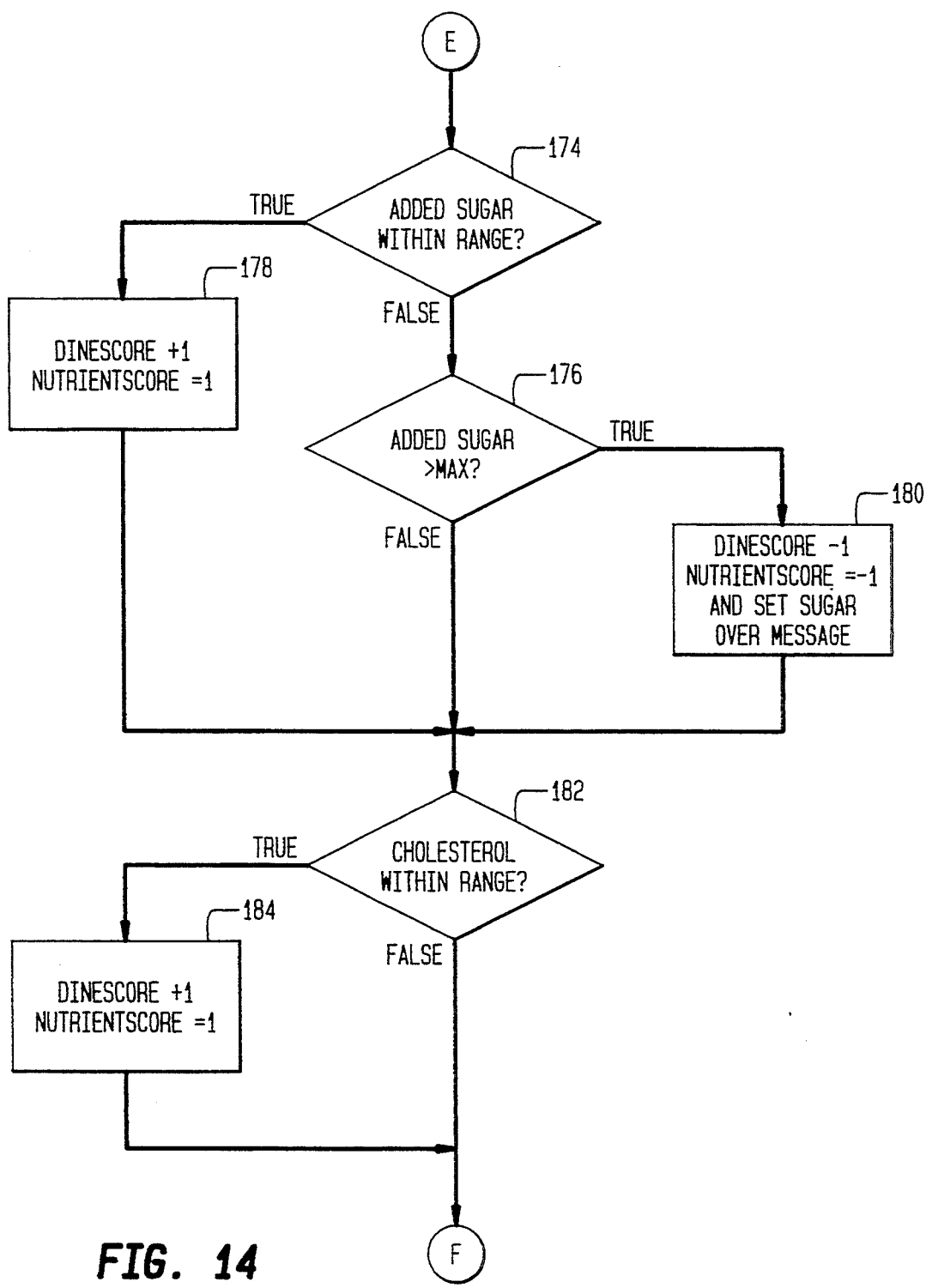

Referring to FIG. 14 sugar and cholesterol content of a diet are evaluated. The system next determines how much added sugar is within an individual's diet [174]. If the amount of added sugar is not within an appropriate range the system next determines if the amount of sugar is greater than the maximum recommended amount [176]. If too much sugar has been consumed a DINE score of "−1" and a nutrient score of "−1" are assigned and a message relating to sugar over consumption is generated [180]. If the amount of sugar consumed is not greater than a maximum recommended amount the system continues on with the next evaluation. Thereafter the system continues with the evaluation. If the amount of added sugar within a diet is within an appropriate range a DINE score of "+1" and a nutrient score of "+1" [178] are assigned and the system continues to the next evaluation.

The amount of cholesterol consumed is next evaluated [182]. If the amount of cholesterol is within an appropriate range a DINE score of "+1" and a nutrient score of "+1" are assigned [184]. If the amount of cholesterol is not within an appropriate range the system continues on the next evaluation.

Figure 15:
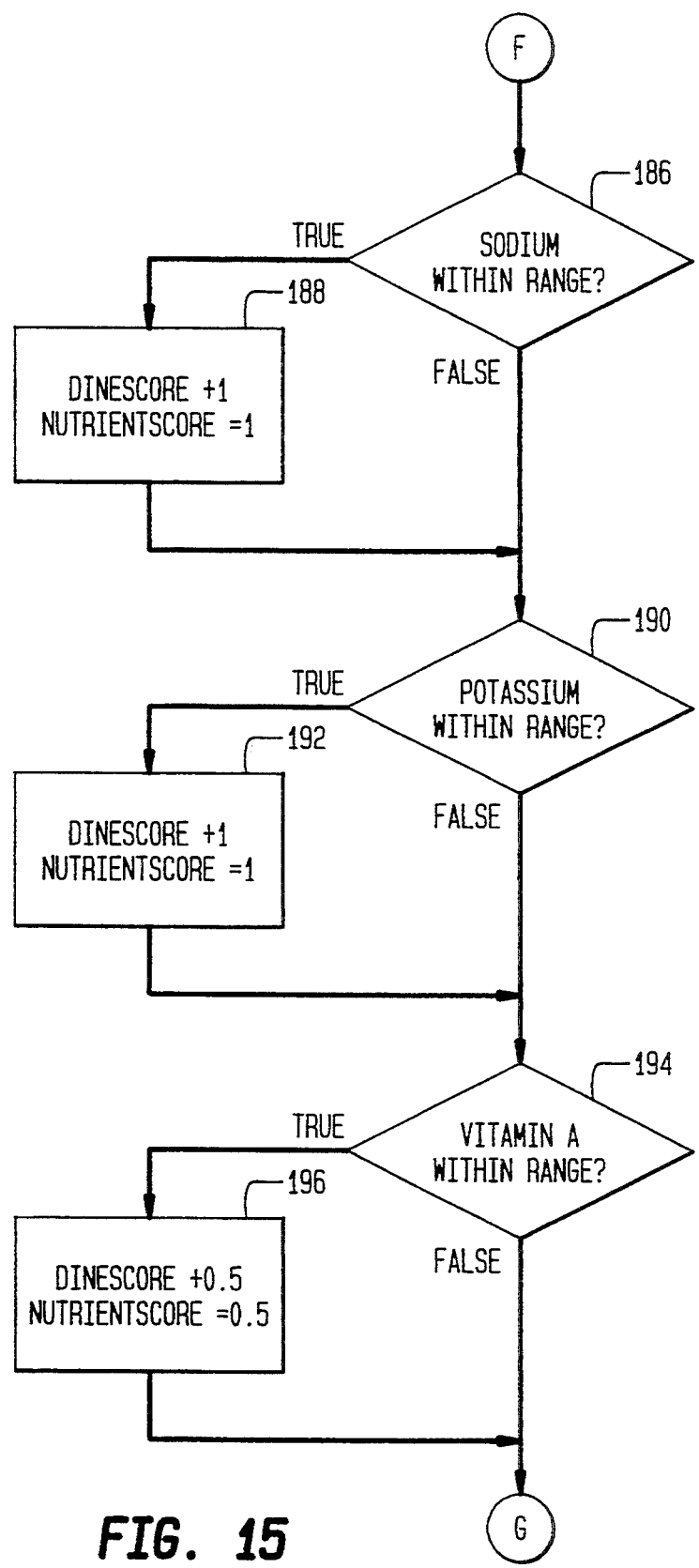

Referring to FIG. 15 the system next determines if the amount of sodium consumed in the diet is within an appropriate range [186]. If sodium consumption is within the approved range a DINE score of "+1" and a nutrient score of "+1" are assigned [188] and the system continues with the evaluation. If sodium consumption is not within an appropriate range the system continues with the evaluation.

The system evaluates if the amount of potassium consumed is within an appropriate range [190]. If the amount of potassium consumed is appropriate a DINE score of "+1" and a nutrient score of "+1" are assigned [192]. If the amount of potassium consumed is not within an appropriate range the system continues on to the next evaluation.

The system next evaluates if the amount of vitamin A is within an appropriate range [194]. If the amount of vitamin A consumed is within an appropriate range a DINE score of "+0.5" and a nutrient score of "+0.5" are assigned [196]. Thereafter the system continues with the evaluation. If amount of vitamin A consumed is not within an appropriate range the system continues with its evaluation.

Figure 16:
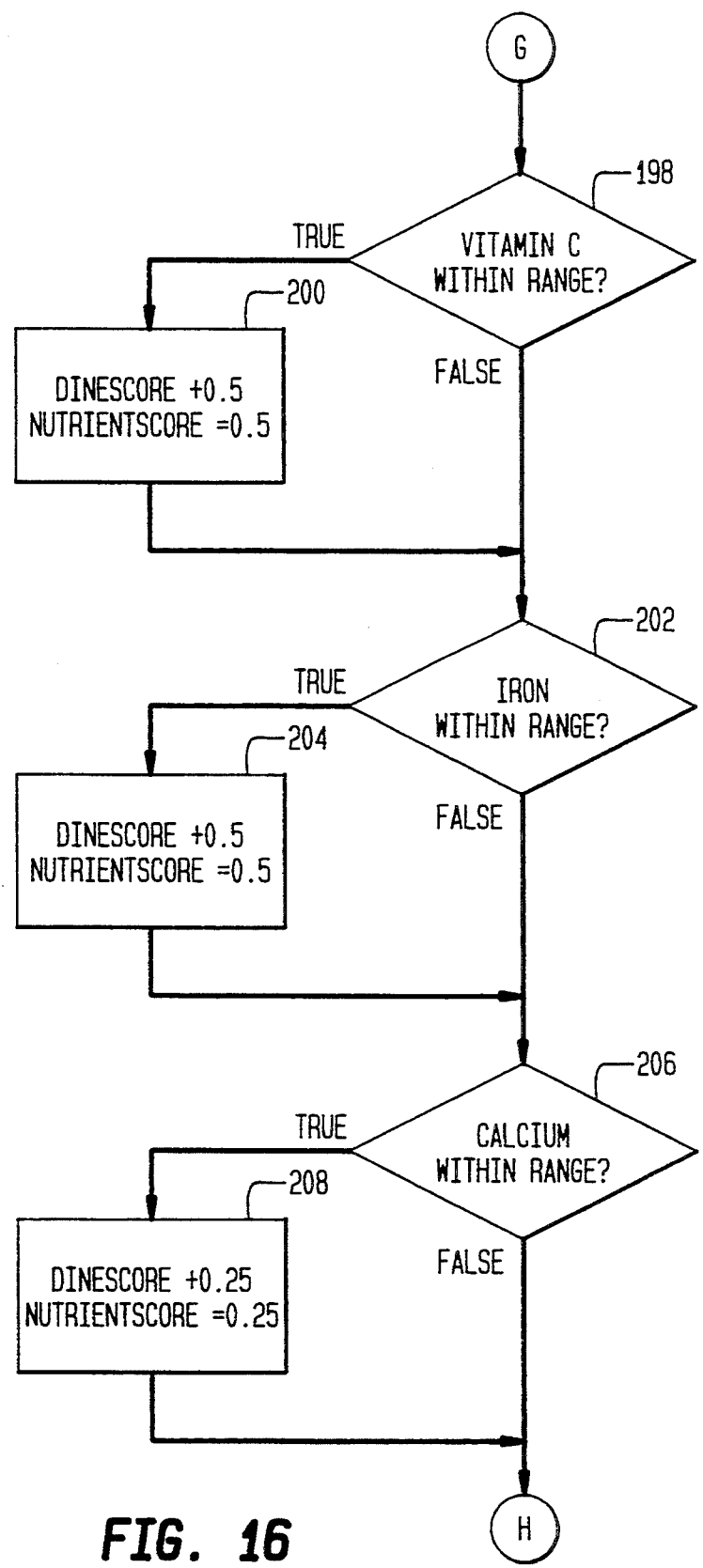

Referring to FIG. 16 evaluation of vitamin C, iron and calcium consumption is described. If vitamin C is determined to be within an appropriate range [198] a DINE score of "+0.5" and a nutrient score of "+0.5" are assigned [200]. Thereafter the system continues on with the next evaluation. If the vitamin C consumed is not within an appropriate range the system continues on to the next evaluation.

The system next determines if the amount of iron consumed is within an appropriate range [202]. If the amount of iron consumed is within the range recommended a DINE score of "+0.5" and a nutrient score of "+0.5" are assigned [204]. If the amount of iron consumed is not within an appropriate range the system continues on to the next evaluation.

Figure 17:
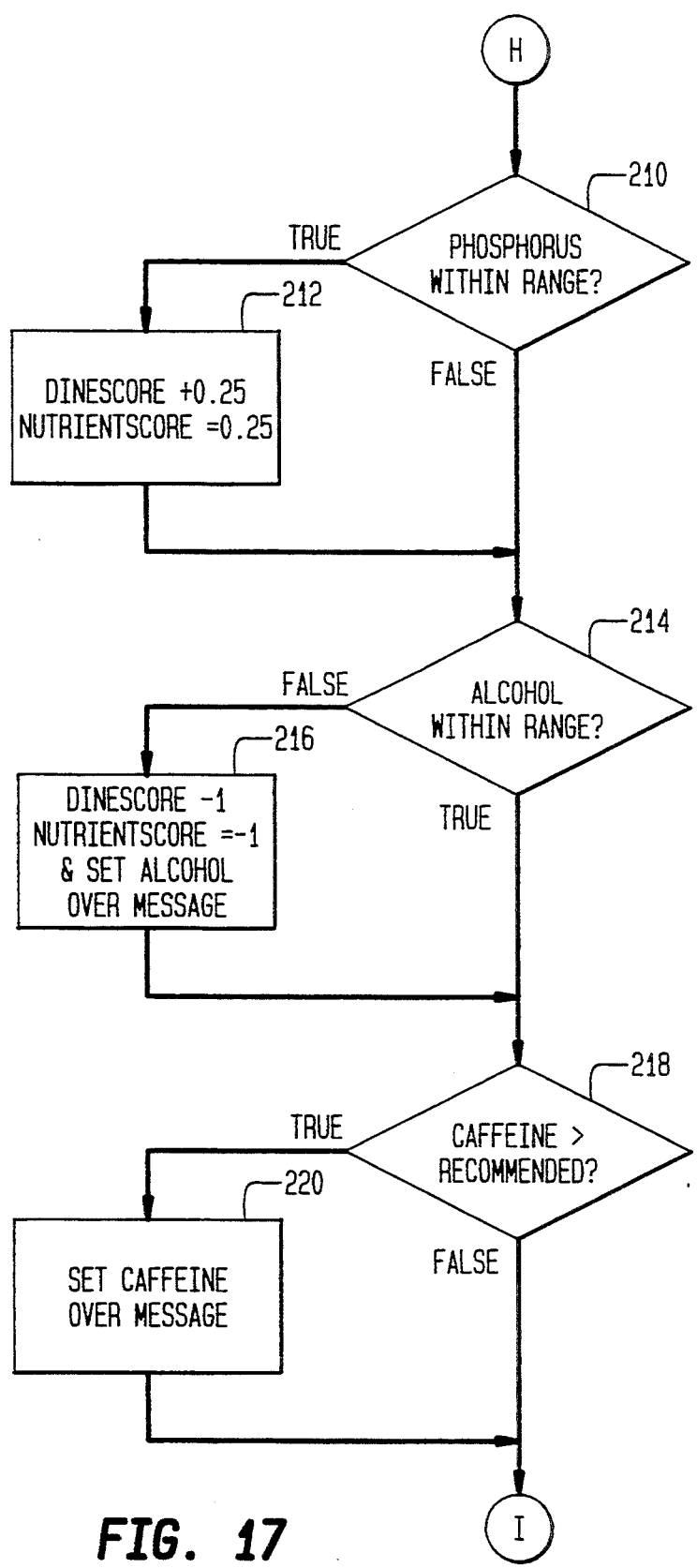

The system next determines if the amount of calcium is appropriate. If the amount of calcium consumed is within an appropriate range [206] a DINE score of "+0.25" and a nutrient score of "+0.25" are assigned [208]. Thereafter the system continues with the evaluation. If the amount of calcium consumed is not within range the system continues on to evaluation of the next nutrient, Referring to FIG. 17 the system next determines if the amount of phosphorus consumed is within an appropriate range [210]. If the amount consumed is within range a DINE score of "+0.25" and a nutrient score of "+0.25" are assigned [212]. The system thereafter continues with its evaluation. If the amount of phosphorus consumed is not within the appropriate range the system continues with the next evaluation.

The system next evaluates the alcohol consumption of the individual [214]. If the amount of alcohol consumed is not within an appropriate range a DINE score of "−1" and a nutrient score of "−1" are assigned [216] and a alcohol over consumption message is created. Thereafter the system continues with the evaluation. If the amount of alcohol consumed is within an appropriate range the system continues to the next evaluation.

The system next determines if the amount of caffeine is in excess of a recommended amount [218]. If the amount of caffeine consumed is over the recommended amount a caffeine over consumption message is created [220] and the system continues with its evaluation. If the amount of caffeine consumed is within the recommended amount the system continues with its evaluation.

Figure 18:
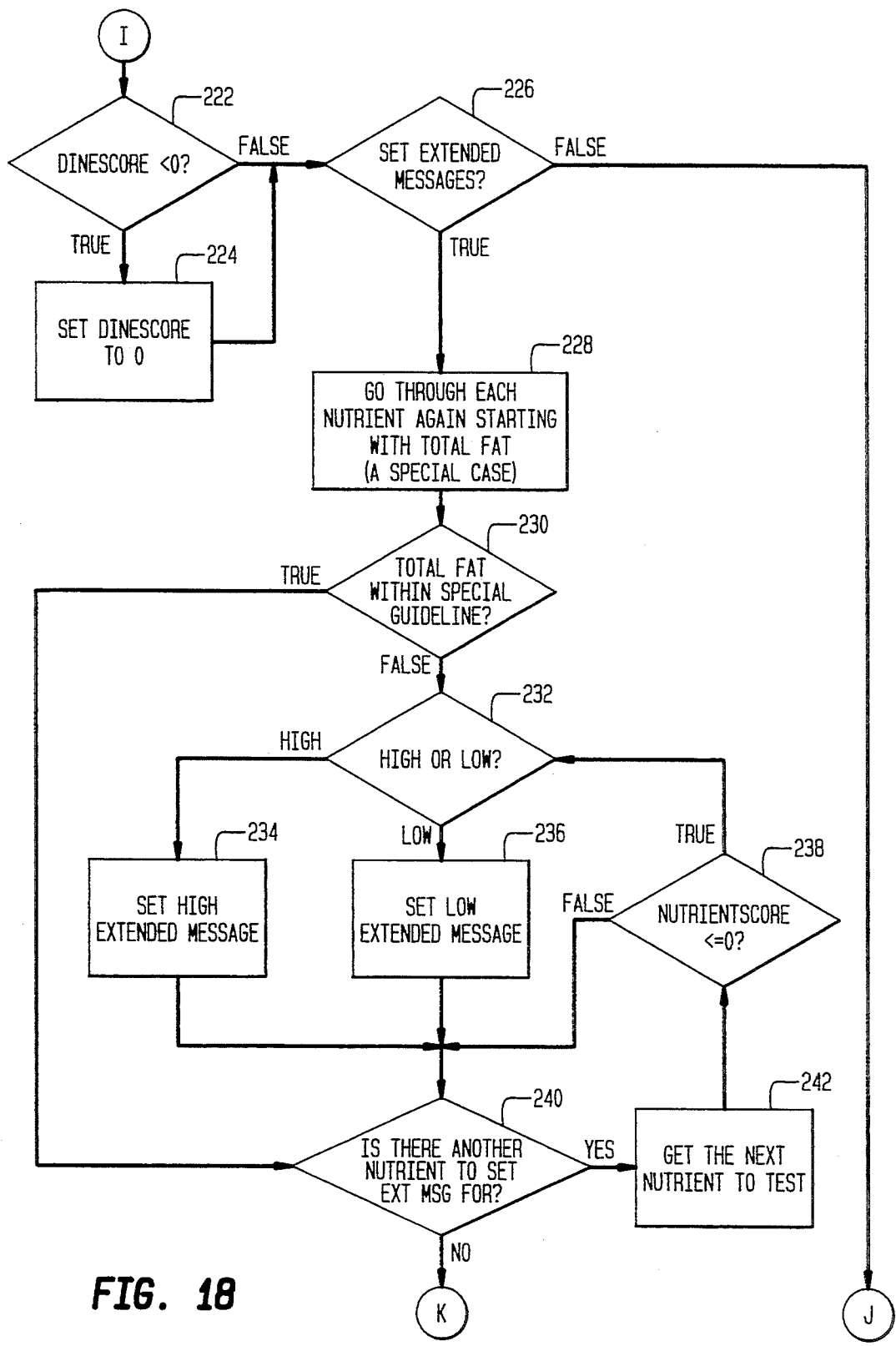

Referring to FIG. 18 the system next determines if a score of less than "0" has been tabulated for all of the evaluations done to this point [222]. If the DINE score is less than "0" the system automatically sets a DINE score equal to "0" [224] and continues with the output of information to the user. If the DINE score is greater than "0" the system continues with providing output to the user.

Figure 19:
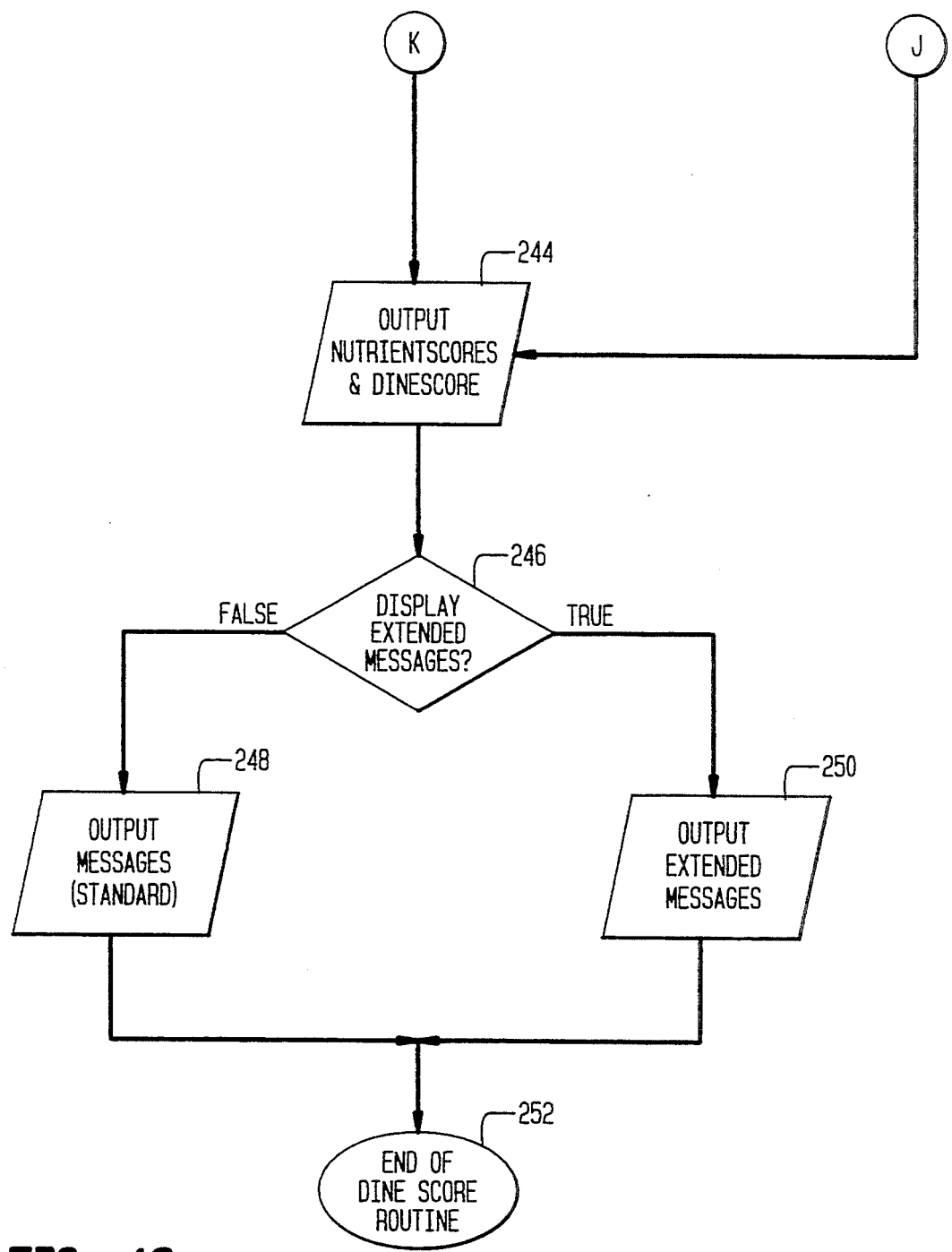

At this stage of the evaluation the user has a series of messages which can be displayed. The system first determines if it has been instructed to provided extended messages to the user [226]. Referring to FIG. 19, if the system has not been set to provided extended messages the system proceeds to the output of nutrient scores and DINE scores [244]. If, however, extended messages are to be given to the user the system proceeds to process those messages. The system first determines whether or not total fat is within a special guideline [230]. If it is within a special guideline the system next inquires whether more nutrients are to be evaluated [240]. If the total fat is not within the special guideline the system next determines whether the amount of fat is above the particular guideline [232]. If the amount of fat consumed is too high an extended message relating to the over consumption of fat is created [234]. The system next proceeds to determine whether more nutrients will be evaluated [240]. If more nutrients are to be determined the system then retrieves the next nutrient to test [242] and determines if the nutrient scores is less than or equal to 0 [236]. If this is true the system returns to an evaluation of whether the total amount of fat in the diet is high. [228]. An evaluation continues thereafter. If this is false the system returns to a determination of whether more nutrients will be evaluated [234]. If no further nutrients are to be evaluated the nutrient scores and diet scores are output.

Referring to FIGS. 18 and 19 after nutrient scores and DINE scores are output the extended messages relating to fat content, sodium, sugar, etc. are displayed to determine whether or not such messages are to be displayed [240]. If the messages are to be displayed they are output to the user [244] on the computer screen, via a printer, or through some other output means. If extended messages are necessary [246], they are to be output at this time [250]. If the extended messages are not to be displayed standard messages are output to the user relating to the diet [248]. After messages are displayed the DINE score routine is terminated [252].

I claim:

1. A computer system for evaluating and analyzing a user's diet, comprising:
   (a) a computing device having a memory;
   (b) an input device for entering information regarding the user's actual dietary intake into the memory;
   (c) a data base in the memory for storing the information;
   (d) a nutrient base in the memory for storing consensus dietary guidelines relative to nutrients consumed by the user;
   (e) a knowledge base in the memory having rules for manipulating the information in the data base to provide an organized historical record of the user's dietary intake and a recommended future diet for the user;
   (f) an application program, for execution in the computing device, for applying the rules in the knowledge base to the information in the data base and the guidelines in the nutrient base and for generating the organized historical record and the recommended future diet;
   (g) a result base in the memory for storage of the organized historical record and the recommended future diet by the application program; and
   (h) means for presenting the contents of the result base to the user, under the direction of the application program;
   (i) the organized historical record including an analysis of the user's actual dietary intake categorized according to predictor nutrients; and
   (j) the recommended future diet including a listing of particular foods suggested for consumption by the user.

2. The computer system of claim 1, wherein the means for presenting the contents of the result base is a display device.

3. The computer system of claim 1, wherein the means for presenting the contents of the result base is a printer.

4. The computer system of claim 1, wherein:
   (a) the application program further compares the contents of the data base to the content of the nutrient base and generates a message for each nutrient consumed by the user, the message stating whether the estimated consumption by the user was below, in excess, or within the guidelines stored in the nutrient base; and
   (b) each message is stored in the result base.

5. An apparatus for evaluating and analyzing a user's diet comprising:
   (a) means for recording information regarding a user's historical dietary intake;
   (b) means for entering the information into a computer;
   (c) means for evaluating, with the aid of the computer, the historical dietary intake to estimate actual amounts of nutrients consumed by the user for a time period;
   (d) logic means for comparing the estimate of actual amounts of nutrients consumed by the user for the time period to recommended ranges of predictor nutrient consumption for the time period; and
   (e) output means for generating, based on the information entered and the comparison of the estimate of actual ranges of nutrients consumed by the user for the time period to the recommended amounts of predictor nutrient consumption for the time period, a dietary intake plan which, if complied with, would make the user's estimate of actual amounts of nutrients consumed for the time period correlate more precisely with the recommended amounts of predictor nutrient consumption for the time period;

f) the dietary intake plan listing particular foods suggested for consumption by the person.

6. The apparatus of claim 5 wherein the output means further generates messages stating whether the estimate of actual amounts of nutrients consumed by the user was within or outside the recommended ranges of nutrient consumption.

7. A method of evaluating a person's dietary nutritional intake, comprising the steps of:
   a) recording information regarding the person's complete actual dietary intake;
   b) entering said information into a computer;
   c) evaluating, with the aid of the computer, the person's complete actual dietary intake to estimate actual amounts of nutrients consumed by the person for a particular time period;
   d) comparing, with the aid of the computer, the estimate of actual amounts of nutrients consumed by the person for the particular time period with a recommended range of amounts of nutrient consumption for the particular time period; and
   e) generating, based on the information entered and the comparison of the estimate of actual amounts of nutrients consumed by the person for the particular time period with the recommended amounts of nutrient consumption for the particular time period, a dietary intake plan which, if complied with, would make said person's said estimate of actual amounts of nutrients consumed for said particular time period correlate more precisely with said recommended range of amounts of nutrient consumption for said particular time period;
   f) the dietary intake plan listing particular foods suggested for consumption by the person; and
   g) wherein the step of evaluating the person's historical dietary intake includes the step of manipulating the person's actual dietary intake to provide an organized historical record of the person's dietary intake, the organized historical record of the person's dietary intake providing an analysis of the person's actual dietary intake categorized according to predictor nutrients.

8. The method of claim 7, in which the predictor nutrients are selected from the group of nutrients consisting of protein, saturated fat, monounsaturated fat, polyunsaturated fat, complex carbohydrates, dietary fiber, sugar, cholesterol, sodium, potassium, vitamin A, vitamin C, iron, calcium, and phosphorus.

9. The method of either claim 7 or claim 8, in which said recommended amounts of nutrient consumption are derived from dietary intake guidelines issued nationally within the United States of America.

10. The method of claim 7, further including the step of generating, based on the information entered and the comparison of the estimate of actual amounts of nutrients consumed by the person for the particular time period with the recommended amounts of nutrient consumption for the particular time period, a dietary intake score which indicates a degree to which the person's organized historical record correlates with the recommended amounts of nutrient consumption for the particular time period.

* * * * *